US012005234B2

(12) United States Patent
Bazargan et al.

(10) Patent No.: US 12,005,234 B2
(45) Date of Patent: Jun. 11, 2024

(54) BACKUP NOTIFICATIONS IN A MEDICAL DEVICE SYSTEM

(71) Applicant: MEDTRONIC MINIMED, INC., Northridge, CA (US)

(72) Inventors: Afshin Bazargan, Simi Valley, CA (US); Michael Ivey, Los Angeles, CA (US); Virgilio Macion, Simi Valley, CA (US); Ali Dianaty, Porter Ranch, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 0 days.

(21) Appl. No.: 17/983,174

(22) Filed: Nov. 8, 2022

(65) Prior Publication Data
US 2023/0068793 A1    Mar. 2, 2023

Related U.S. Application Data

(63) Continuation of application No. 16/554,504, filed on Aug. 28, 2019, now abandoned.

(51) Int. Cl.
*G06F 11/07* (2006.01)
*A61M 5/142* (2006.01)
(Continued)

(52) U.S. Cl.
CPC ...... *A61M 5/1723* (2013.01); *A61M 5/14244* (2013.01); *G06F 11/0757* (2013.01);
(Continued)

(58) Field of Classification Search
CPC ............. G06F 11/0757; G06F 11/0793; G06F 11/142; G06F 11/1438; G06F 11/1441;
(Continued)

(56) References Cited

U.S. PATENT DOCUMENTS

| 4,562,751 A | 1/1986 | Nason et al. |
| 4,685,903 A | 8/1987 | Cable et al. |

(Continued)

FOREIGN PATENT DOCUMENTS

| EP | 4120285 A1 | 1/2023 |
| WO | 2021041362 A1 | 3/2021 |
| WO | 2021067767 A1 | 4/2021 |

OTHER PUBLICATIONS

EP Extended European Search report dated Dec. 15, 2022 in Application No. EP22193010.
(Continued)

*Primary Examiner* — Matthew M Kim
*Assistant Examiner* — Kyle Emanuele
(74) *Attorney, Agent, or Firm* — Weaver Austin Villeneuve & Sampson LLP

(57) ABSTRACT

Techniques disclosed herein relate generally to notification generation in a medical device system. In some embodiments, the techniques involve generating a first notification via a medical application executing on a first device, determining that the first notification was not acknowledged within a predetermined time frame, and causing generation of a second notification at a medical device carried by a user to notify the user that the first notification has not been acknowledged.

19 Claims, 7 Drawing Sheets

(51) Int. Cl.
  *A61M 5/172* (2006.01)
  *G06F 11/14* (2006.01)
  *G16H 20/17* (2018.01)
  *G16H 40/67* (2018.01)

(52) U.S. Cl.
  CPC ........ *G06F 11/0793* (2013.01); *G06F 11/142* (2013.01); *G06F 11/1438* (2013.01); *G06F 11/1441* (2013.01); *G16H 20/17* (2018.01); *G16H 40/67* (2018.01); *A61M 2005/14208* (2013.01); *A61M 2005/14272* (2013.01); *A61M 2005/1726* (2013.01); *A61M 2205/52* (2013.01); *A61M 2230/201* (2013.01)

(58) Field of Classification Search
  CPC ............ A61M 5/1723; A61M 5/14244; A61M 2005/14272; A61M 2005/1726; A61M 2205/52; A61M 2230/201; G16H 20/17
  See application file for complete search history.

(56) References Cited

U.S. PATENT DOCUMENTS

| | | | |
|---|---|---|---|
| 4,755,173 A | 7/1988 | Konopka et al. |
| 5,080,653 A | 1/1992 | Voss et al. |
| 5,097,122 A | 3/1992 | Colman et al. |
| 5,391,250 A | 2/1995 | Cheney et al. |
| 5,485,408 A | 1/1996 | Blomquist |
| 5,505,709 A | 4/1996 | Funderburk et al. |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Vanantwerp et al. |
| 6,017,328 A | 1/2000 | Fischell et al. |
| 6,088,608 A | 7/2000 | Schulman et al. |
| 6,119,028 A | 9/2000 | Schulman et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,485,465 B2 | 11/2002 | Moberg et al. |
| 6,544,212 B2 | 4/2003 | Galley et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,589,229 B1 | 7/2003 | Connelly et al. |
| 6,591,876 B2 | 7/2003 | Safabash |
| 6,641,533 B2 | 11/2003 | Causey, III et al. |
| 6,659,980 B2 | 12/2003 | Moberg et al. |
| 6,736,797 B1 | 5/2004 | Arsen et al. |
| 6,740,072 B2 | 5/2004 | Starkweather et al. |
| 6,749,587 B2 | 6/2004 | Flaherty |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van et al. |
| 6,817,990 B2 | 11/2004 | Yap et al. |
| 6,827,702 B2 | 12/2004 | Lebel et al. |
| 6,932,584 B2 | 8/2005 | Gray et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,323,142 B2 | 1/2008 | Pendo et al. |
| 7,399,277 B2 | 7/2008 | Saidara et al. |
| 7,402,153 B2 | 7/2008 | Steil et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van et al. |
| 8,353,829 B2 | 1/2013 | Say et al. |
| 8,474,332 B2 | 7/2013 | Bente, IV et al. |
| 8,674,288 B2 | 3/2014 | Hanson et al. |
| 2004/0121767 A1 | 6/2004 | Simpson et al. |
| 2007/0123819 A1 | 5/2007 | Mernoe et al. |
| 2010/0160861 A1 | 6/2010 | Causey, III et al. |
| 2011/0050428 A1 | 3/2011 | Istoc |
| 2014/0066889 A1 | 3/2014 | Grosman et al. |
| 2014/0187890 A1* | 7/2014 | Mensinger ........ A61B 5/14532 600/365 |
| 2014/0253323 A1* | 9/2014 | Berven ............... G08B 21/02 340/539.12 |
| 2014/0288947 A1* | 9/2014 | Simpson .............. G16H 10/60 705/2 |
| 2016/0034658 A1 | 2/2016 | Berman et al. |
| 2016/0119210 A1* | 4/2016 | Koehler .............. G16H 20/60 370/245 |
| 2017/0131993 A1* | 5/2017 | Salameh ............ G06F 9/44505 |
| 2017/0286194 A1 | 10/2017 | Morris et al. |
| 2018/0369479 A1 | 12/2018 | Hayter et al. |
| 2019/0173885 A1* | 6/2019 | Kamath .............. A61B 5/686 |
| 2020/0250939 A1* | 8/2020 | Mears ................. G16H 10/60 |
| 2021/0060244 A1 | 3/2021 | Bazargan et al. |

OTHER PUBLICATIONS

International Preliminary Report on Patentability dated Mar. 10, 2022, in PCT Application No. PCT/US2020/047718.
International Search Report and Written Opinion dated Nov. 11, 2020, in Application No. PCT/US2020/047718.

(56) References Cited

OTHER PUBLICATIONS

U.S Non-Final Office Action dated Aug. 9, 2022, in U.S. Appl. No. 16/554,504.

* cited by examiner

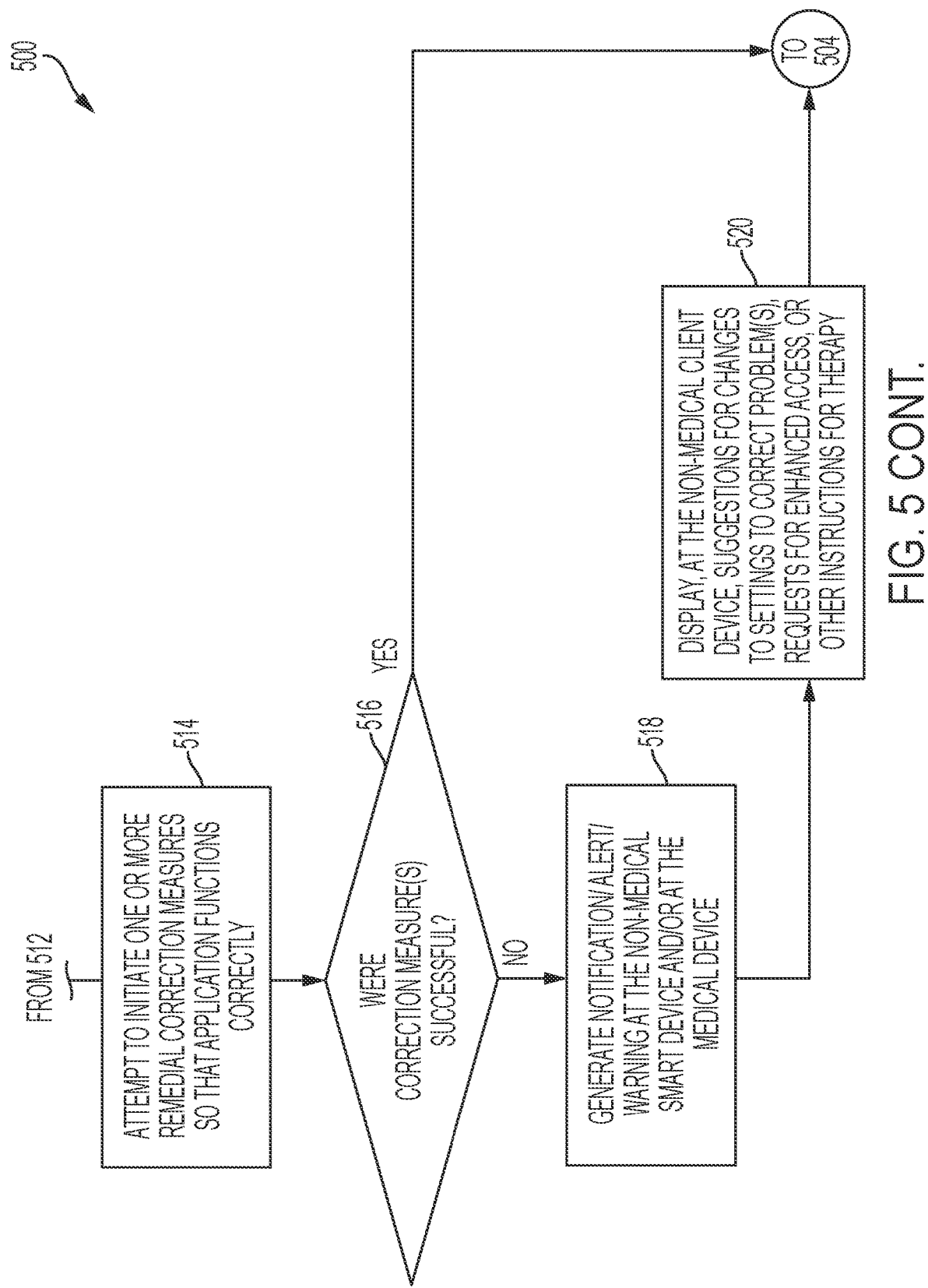

BACKUP NOTIFICATIONS IN A MEDICAL DEVICE SYSTEM

CROSS-REFERENCE TO RELATED APPLICATIONS

This application is a continuation of U.S. patent application Ser. No. 16/554,504, filed Aug. 28, 2019, entitled "METHOD AND SYSTEM FOR VERIFYING WHETHER A NON-MEDICAL CLIENT DEVICE IS OPERATING CORRECTLY WITH A MEDICAL DEVICE CONTROLLED BY THE NON-MEDICAL CLIENT DEVICE AND CAUSING A NOTIFICATION TO BE GENERATED," which is herein incorporated by reference in its entirety for all purposes.

TECHNICAL FIELD

Techniques disclosed herein relate generally to notification generation in medical device systems.

BACKGROUND

Wireless devices, such as cellular telephones, mobile computers, personal digital assistants, digital media players, portable video game devices, and the like, and related wireless communication techniques and protocols have become ubiquitous in modern society. More recently, portable medical devices having wireless data communication capabilities are becoming increasingly popular, especially for patients that have conditions that must be monitored on a continuous or frequent basis. For example, diabetics are usually required to modify and monitor their daily lifestyle to keep their body in balance, in particular, their blood glucose ("BG") levels. Individuals with Type 1 diabetes and some individuals with Type 2 diabetes use insulin to control their BG levels. To do so, diabetics routinely keep strict schedules, including ingesting timely nutritious meals, partaking in exercise, monitoring BG levels daily, and adjusting and administering insulin dosages accordingly. Diabetics may utilize wireless medical devices that are deployed in a network environment in a manner that facilitates data communication between two or more separate devices.

In the past, on-body medical devices, such as fluid infusion device (or infusion pump) and sensing arrangement (e.g., continuous glucose sensors), could be controlled using a custom controller device (CCD). Today, there is a growing trend towards controlling personal medical devices, such as insulin infusion devices that are worn by a patient, using a non-medical device such as a patient's smart phone, laptop or tablet. On-body medical devices can now be communicated with and controlled using a non-medical smart device (e.g., smartphone, tablet). One advantage of this approach is that it can eliminate the need for a patient to possess and use another distinct control device. This can make the cost of ownership lower. In addition, patients can be discreet in managing their disease, and use a familiar user interface and form-factor which shortens the learning curve. This can also provide connectivity to back-end systems (e.g., cloud-based systems) that are used to monitor patients and control delivery of medication to a patient. Non-medical smart devices can upload data for analysis by health care providers (HCPs) and AI-based systems. Non-medical smart devices can also receive regular updates to therapy management software. For instance, these updates can update medical control application software (or key parameters thereof) to customize and improve therapy. Connectivity also provides the means to alert caregivers and HCPs in emergency situations when concerning trends are present. A medical control application can also use health related data from the non-medical smart device and other apps/systems to improve therapy for the patient.

A number of insulin pump systems are designed to deliver accurate and measured doses of insulin via infusion sets (an infusion set delivers the insulin through a small diameter tube that terminates at a cannula inserted under the patient's skin). In lieu of a syringe, the patient can simply activate the insulin pump to administer an insulin bolus as needed, for example, in response to the patient's current BG level. A patient can measure his BG level using a BG measurement device, such as a test strip meter, a continuous glucose measurement system, or the like. BG measurement devices use various methods to measure the BG level of a patient, such as a sample of the patient's blood, a sensor in contact with a bodily fluid, an optical sensor, an enzymatic sensor, or a fluorescent sensor. When the BG measurement device has generated a BG measurement, the measurement is displayed on the BG measurement device. A continuous glucose monitoring system can monitor the patient's sensor glucose (SG) level (e.g., subcutaneous tissue glucose level) in real-time. This allows delivery of insulin to be calculated in real-time with dosage calculated in a software algorithm based on measured sensor glucose level, or a closed-loop algorithm.

The insulin pump, continuous glucose monitoring (CGM) device, and other devices, such as a smartphone and a Blood Glucose Monitor (BGM), can be different parts of an insulin infusion system. The various devices that are part of the insulin infusion system can form a wireless body area network that can be used, for example, to exchange monitor and therapy (control) data among multiple medical devices that are either worn on or near a patient's body. For instance, therapy data such as measured glucose values (SG values) and therapy settings (parameters for bolus delivery) can be transferred wirelessly among devices within the body area network. Insulin pumps and CGM devices may also be configured to communicate with remote control devices, monitoring or display devices, BG meters, and other devices associated with such an infusion system. For example, a CGM sensor may include or cooperate with a wireless radio frequency ("RF") transmitter that communicates with other devices that are part of an infusion system such as a handheld remote control (also called a command control device (CCD)) that communicates with the infusion pump device using wireless communication technologies such as classical Bluetooth® (BT) or Bluetooth Low Energy® (BLE) technologies.

The insulin infusion device and the smartphone can both include displays and different types of alarms to alert a user when they are not operating correctly. For instance, with respect to the insulin infusion device, if a microcontroller of the insulin infusion device fails, a notification (e.g., a message on a display, an audible or visual alarm or other type of alert such as a vibration) can be activated to inform the user that their insulin infusion device is not operating correctly.

While using non-medical devices such smartphones can provide a number of advantages, one risk from the perspective of medical device manufacturers is that a smartphone or other smart devices are a relatively open platform and not as controllable as a medical device.

Accordingly, it is desirable to provide a medical device system, such as an insulin infusion system, that can verify whether a non-medical client device (e.g., smartphone or other smart device) is operating correctly with a wearable medical device (e.g., insulin infusion device) that is controlled by the non-medical client device. It would also be desirable to reduce risk associated with using a smartphone. Furthermore, other desirable features and characteristics will become apparent from the subsequent detailed description and the appended claims, taken in conjunction with the accompanying drawings and the foregoing technical field and background.

BRIEF SUMMARY

Techniques disclosed herein relate generally to notification generation in medical device systems and, more specifically, to methods and medical device systems for generating backup notifications in response to unacknowledged notifications. The techniques may be practiced using a processor-implemented method; a system comprising one or more processors and one or more processor-readable media; and one or more non-transitory processor-readable media According to certain embodiments, the techniques involve generating a first notification via a medical application executing on a first device, determining that the first notification was not acknowledged within a predetermined time frame, and causing generation of a second notification at a medical device carried by a user to notify the user that the first notification has not been acknowledged.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
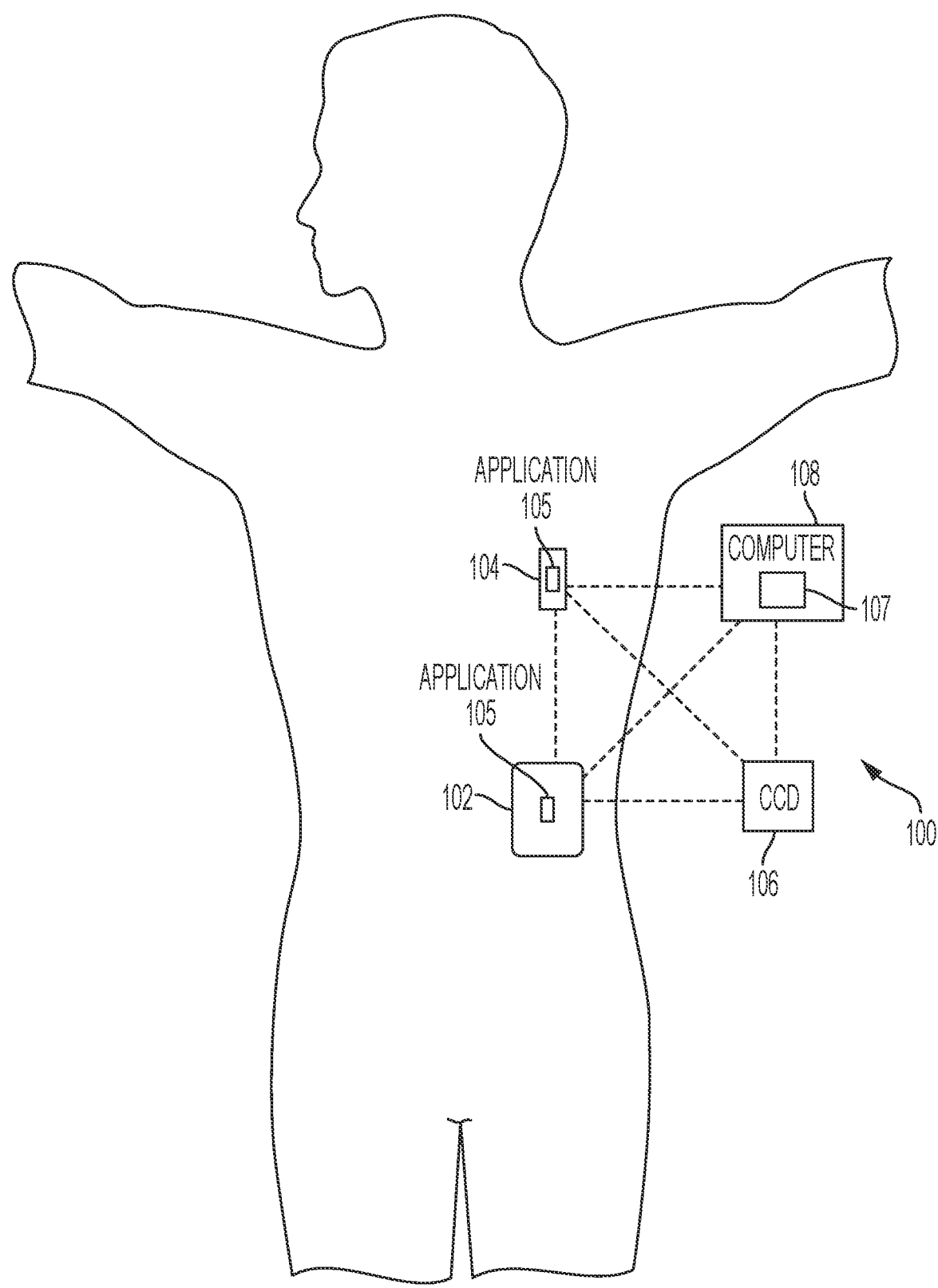
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

When implemented in software, firmware, or processor-readable instructions, various elements of the systems described herein are essentially the code segments or instructions that perform the various tasks. In certain embodiments, the program or code segments are stored in a tangible processor-readable medium, which may include any medium that can store or transfer information. Examples of a non-transitory and processor-readable medium include an electronic circuit, a semiconductor memory device, a ROM, a flash memory, an erasable ROM (EROM), a floppy diskette, a CD-ROM, an optical disk, a hard disk, or the like.

Exemplary embodiments of the subject matter described herein are implemented in conjunction with medical devices, such as portable electronic medical devices. Although many different applications are possible, the following description focuses on embodiments that incorporate an insulin infusion device (or insulin pump) as part of an infusion system deployment. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Generally, a fluid infusion device includes a motor or other actuation arrangement that is operable to linearly displace a plunger (or stopper) of a fluid reservoir provided within the fluid infusion device to deliver a dosage of fluid, such as insulin, to the body of a user. Dosage commands that govern operation of the motor may be generated in an automated manner in accordance with the delivery control scheme associated with a particular operating mode, and the dosage commands may be generated in a manner that is influenced by a current (or most recent) measurement of a physiological condition in the body of the user. For example, in a closed-loop or automatic operating mode, dosage commands may be generated based on a difference between a current (or most recent) measurement of the interstitial fluid glucose level in the body of the user and a target (or reference) glucose setpoint value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin.

Smart devices (e.g., smartphones) are devices that are available to the general public and have other uses beyond medical applications. Using such non-medical devices as part of a medical device system can provide a number of advantages. However, from the perspective of medical device manufacturers, one concern with using such non-medical devices to control medical devices is their open nature, reliability and security because smart devices are relatively open platforms and not as controllable as a medical device. Other than writing the code for a medical control application that is implemented on a patient's smart device, medical device manufacturers have little control of the patient's smart device to ensure that it is working correctly. For example, the medical device manufacturer does not write the operating system used by the smart device, has no control over installation of the most up-to-date software on the smart device (including the medical control application), cannot control what the user does to settings on the smart device, etc. For example, there is no way to ensure that a patient updates operating system (OS) software and other apps, or that a patient properly configures settings of the non-medical smart device. In addition, the availability of required computing resources on the non-medical smart device can affect functionality of the system. By contrast, because medical devices are designed by device manufacturers there is more control over their operations and settings they are thus considered more reliable.

In addition, users can control operation of their smart device and change settings (e.g., volume settings, wireless communication interface settings), etc. For example, users are responsible for controlling settings of their smart device, what other devices they are connected to, usage of computing resources, updates to the operating system or other application software (including what applications are installed and potentially conflict with a medical control application), etc. A need may arise to notify or alert the user (e.g., when the patient's blood glucose level goes low), but certain settings on the smart device may be set in a way that prevents this from happening. As an example, Bluetooth maybe in use for a phone call, speakers may be in use for listening to music, or the device's volume might be turned off. In short, this open nature of smart devices creates a potential risk that a medical control application executed at the smart device may not operate as intended.

To address these issues a medical device system, such as an insulin infusion system, is provided that can verify whether a non-medical client device (e.g., smartphone or other smart device) is operating correctly with a wearable medical device (e.g., insulin infusion device) that is controlled by the non-medical client device. This system can reduce risk associated with using a smart device such as a smartphone, and increase the likelihood that a patient can continue to get notifications in the event that their smartphone, or the medical control application executed on their smartphone, fails. For instance, the system can allow patients to continue to receive alerts, alarms, and other warnings concerning their medical devices when needed even though their smart device (or non-medical device) may not be communicating them, or even though a medical control application that runs on their smart device is not operating as intended. For example, the system can allow patients to continue to receive alerts, alarms, and other warnings when a battery dies on the patient's smartphone, or when the user switches a communication interface (like a Bluetooth interface) so that it is linked to another device, or when the user turns the volume on smartphone off so that alarms generated by the application are not audible to the patient, or when the medical control application fails to operate as intended for any reason.

In one embodiment, methods, systems and apparatus are provided for verifying whether a non-medical client device is operating correctly with a medical device controlled by the non-medical client device and causing a notification to be generated. The medical device and the non-medical client device can be part of a wireless body area network for a medical device system, namely, an insulin infusion system. In accordance with certain embodiments, the insulin infusion system includes an insulin infusion device configured to deliver insulin to a user, a glucose sensor arrangement, a mobile, non-medical client device such as a smartphone, etc. For example, the non-medical client device can be smartphone, and the medical device can be an insulin infusion device that is configured to be controlled via the medical control application executed at the smartphone.

In one embodiment, an application at the non-medical client device can monitor for occurrence of a trigger event, and when the application at the non-medical client device detects occurrence of the trigger event, the application at the non-medical client device can perform one or more diagnostic checks to verify whether a medical control application at the non-medical client device is operating correctly. For example, in one implementation, the trigger event can be one or more of: receiving an indication that a notification needs to be acknowledged; receiving an indication that a notification needs to be activated; receiving an indication that a notification has been issued; receiving an indication that a timer has expired; and receiving an indication that a counter has a count that exceeds a threshold count. Further, in one implementation, the one or more diagnostic checks can include one or more of: determining whether an operating system version is up to date; determining whether the medical control application is up to date; determining whether settings of the medical control application are correct; determining whether the medical control application is loading properly; and determining whether the medical control application is running properly.

When the application at the non-medical client device determines that the one or more diagnostic checks have failed (e.g., this can mean that the medical control application is not operating correctly), the application can attempt to initiate one or more remedial correction measures to restore the medical control application so that it is operating correctly. The one or more remedial correction measures attempt to correct issues that are causing the non-medical client device to run improperly so that the medical control application will function correctly and have access to required computing resources (e.g., memory, processing, user interfaces, communication interfaces, power sources/supplies, etc.). For example, in one implementation, the remedial correction measures can include one or more of: automatically closing and restarting the medical control application; prompting the user to change restart the medical control application of the non-medical client device when it is determined that the medical control application is not loading or is not running properly; automatically powering the non-medical client device off, automatically restarting non-medical client device and reopening the medical control application; downloading and installing an up-to-date version of the medical control application or an up-to-date version of an operating system when it is determined that the existing versions were not correct; prompting the user to change one or more settings of the medical control application when it is determined that one or more settings of the medical control application are incorrect; and freeing up additional computing resources of the non-medical client device for use by the medical control application when it is determined that the medical control application does not have access to adequate computing resources.

When the one or more remedial correction measures are unsuccessful, the application causes a first notification to be generated via a user interface of the non-medical client device, and can start a counter after causing the notification to be generated. Thereafter, the application at the non-medical client device can regularly determine whether an acknowledgement signal was generated to acknowledge the notification. When a count of the counter exceeds a threshold count and no acknowledgement signal was generated to acknowledge the first notification, the application can cause a second notification to be generated via a second user interface of the medical device. The second notification is used to alert a user that thee first notification generated at the non-medical client device has not been acknowledged so that other remedial measures can be taken at the non-medical client device.

For instance, in one implementation, the application at the non-medical client device can initiate a verification protocol when it detects the occurrence of the trigger event. The verification protocol can include executing diagnostic checks to verify whether the medical control application is functioning properly and has access to adequate computing resources (e.g., processing resources, communication resources, user interface resources, memory resources).

In another embodiment, the application at the non-medical client device can perform a communication link verification process, when the application detects occurrence of the trigger event, to determine whether the non-medical client device has an established communication link to the wearable medical device. When the application at the non-medical client device determines that the non-medical client device does not haves a communication link to the wearable medical device, the application can attempt to establish a communication link between the non-medical client device and the medical device, and if the attempt to establish the communication link is unsuccessful, the application can cause a first notification to be generated via the user interface of the non-medical client device, and/or cause a second notification to be generated via a second user interface of the medical device.

In yet another embodiment, a method is provided for an application on the non-medical device (e.g., smartphone, tablet or laptop) to take control of the insulin pump to issue a notification or an alert (e.g., activate an audio or visual alarm, activate a haptic signal). This provides a way to let a patient know that their non-medical device may not be operating as intended to alert them that some action needs to be taken. In one implementation, a smartphone can periodically check to make sure that an application and/or the smartphone that runs the application are working as required. For example, whenever information indicates that an alarm needs to be issued, a check can be performed to make sure that the application and/or smartphone that runs the application are operating correctly. This way, the system can determine whether everything is connected and working properly so that the user knows if the medical control application is working correctly or as intended. If everything is not connected or working properly, then backup alert system or alarm on the body-worn medical device (e.g., CGM, insulin pump, or both) can be used as a backup to notify the user that the non-medical device or application it is executing is not operating properly or optimally as recommended (e.g., alert the user that the application and/or smartphone that runs the application are not working as required, and/or to alert the user that some action needs to be taken).

Turning now to FIG. 1, one exemplary embodiment of an infusion system 100 includes, without limitation, a fluid infusion device (or infusion pump) 102, a sensing arrangement 104, a command control device (CCD) 106, and a computer 108. The components of an infusion system 100 may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. Pat. No. 8,674,288, the subject matter of which is hereby incorporated by reference in its entirety.

In the illustrated embodiment of FIG. 1, the infusion device 102 is designed as a portable medical device suitable for infusing a fluid, a liquid, a gel, or other medicament into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological condition, such as a blood glucose level, or the like, of the user, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the user.

In some embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the user's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be used for determining glucose levels in the blood and/or body fluids of the user without the use of, or necessity of, a wire or cable connection between the infusion device 102 and the sensing arrangement 104 and/or the CCD 106.

In some embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402,153 or United States Patent Application Publication No. 2014/0066889, all of which are incorporated herein by reference in their entirety. In such embodiments, the sensing arrangement 104 is configured to sense or measure a condition of the user, such as, blood glucose level or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example only when the user is asleep or awake.

Figure 2:
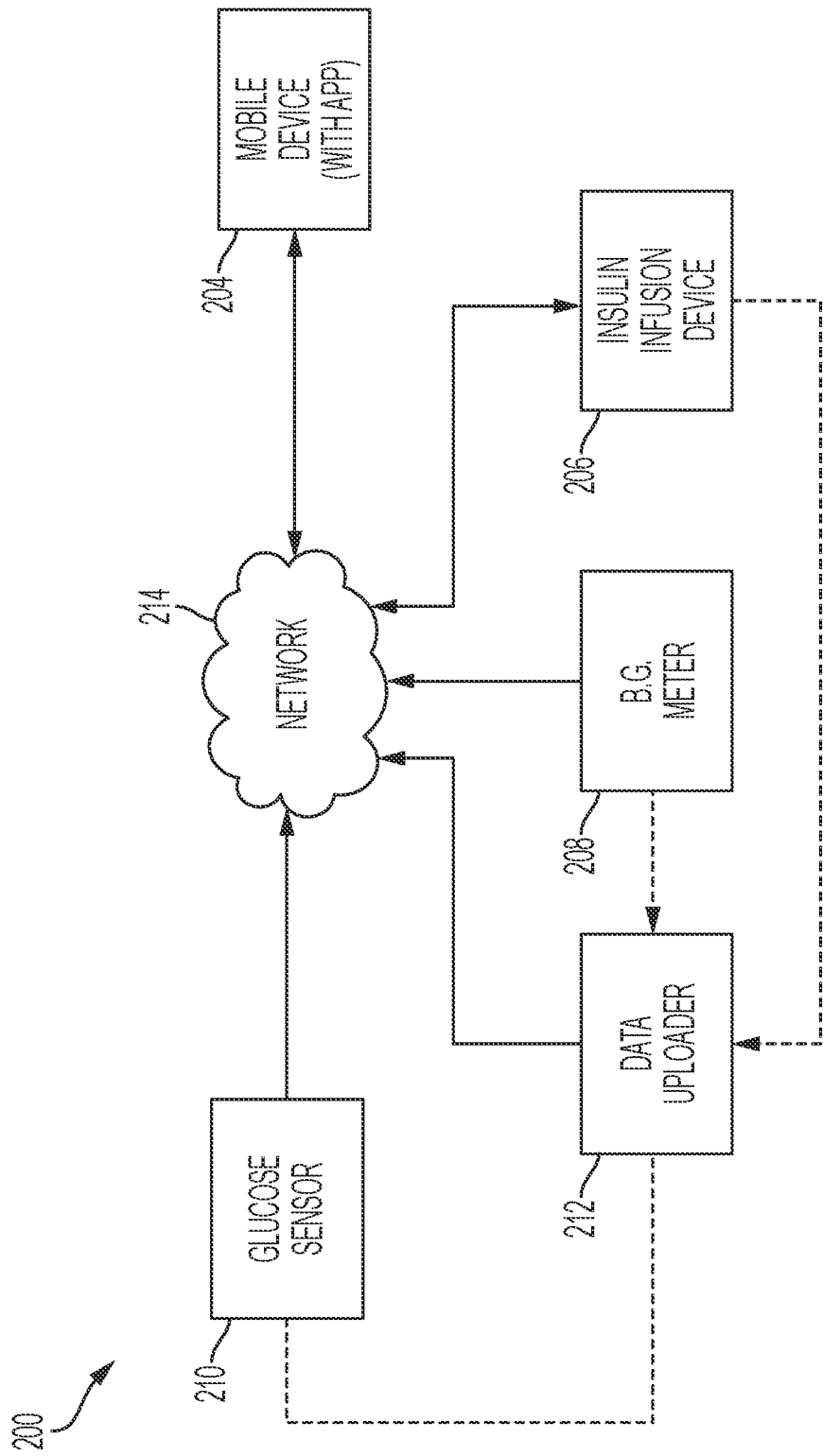
FIG. 2 is a simplified block diagram representation of an exemplary embodiment of a communication system.

FIG. 2 is a simplified block diagram representation of an exemplary embodiment of a communication system 200 that is suitably configured to support the techniques and methodologies described in more detail below. The system 200 supports users of insulin infusion devices, and performs various techniques and methods to help users (patients, caregivers, healthcare providers, parents, etc.) manage the use of insulin infusion devices. It should be appreciated that FIG. 2 depicts one possible implementation of a communication system, and that other arrangements, architectures, and deployments can be provided if so desired. The system 200 (which has been simplified for purposes of illustration) generally includes or cooperates with the following components, without limitation: a mobile device 204; an insulin infusion device 206; a blood glucose meter 208; a continuous glucose sensor 210; and an optional data uploader 212. The mobile device 204 is a client device that is owned or operated by the user, i.e., a diabetic patient. The insulin infusion device 206, the blood glucose meter 208, and the glucose sensor 210 are components of an insulin infusion system that is used by the patient to treat diabetes. The system 200 may also include or cooperate with the optional data uploader component 212.

The various components of the system 200 can be used to collect and analyze input data for the patient that can originate from various sources, including an insulin infusion device, a glucose sensor or meter, a mobile device operated by a user of the insulin infusion device, or other components or computing devices that are compatible with the system, such as a data uploader. These and other alternative arrangements are contemplated by this disclosure. To this end, some embodiments of the system may include additional devices and components that serve as data sources, data processing units, etc. For example, the system may include any or all of the following elements, without limitation: computer devices or systems; patient monitors; healthcare provider systems; data communication devices; and the like. It should be appreciated that the insulin infusion device 206 can be an optional component in some applications (for example, for Type 2 diabetes patients). For such applications, another diabetes management device and/or the mobile device 204 can function in an equivalent manner to support the system 200.

At a minimum, the mobile device 204 is communicatively coupled to a network 214. In certain embodiments, the insulin infusion device 206, the blood glucose meter 208, and/or the continuous glucose sensor 210 are also communicatively coupled to the network 214 to facilitate the uploading of relevant data to a remote server system (not illustrated). Alternatively, or additionally, the insulin infusion device 206, the blood glucose meter 208, and the continuous glucose sensor 210 provide relevant data to the data uploader component 212, which in turn uploads the data to other systems (not illustrated) via the network 214.

FIG. 2 depicts the network 214 in a simplified manner. In practice, the system 200 may cooperate with and leverage any number of wireless and any number of wired data communication networks maintained or operated by various entities and providers. Accordingly, communication between the various components of the system 200 may involve multiple network links and different data communication protocols. In this regard, the network 214 can include or cooperate with any of the following, without limitation: a local area network; a wide area network; the Internet; a personal area network; a cellular communication network; a satellite communication network; a video services or television broadcasting network; a network onboard a vehicle; or the like. In addition, the various components can also communicate directly with each other using NFMI radio communications; NFeMI radio communications, BLE® communications, classical Bluetooth® (BT) communications, WLAN (or "Wi-Fi") communications, or indirectly with each other using WLAN or cellular communications, as will be described below. The components of the system may be suitably configured to support a variety of wireless and wired data communication protocols, technologies, and techniques as needed for compatibility with the network 214.

The mobile device 204 can be realized using a variety of different device platforms. For example, the mobile device 204 can be implemented as any of the following, without limitation: a cellular telephone or smartphone; a portable computer (e.g., a laptop, a tablet, or a netbook computer); a portable media player; a portable video game device; a portable medical device; a navigation device such as a global positioning system (GPS) device; a wearable computing device; an electronic toy or game; etc. In accordance with certain exemplary embodiments, the mobile device 204 supported by the system 200 is implemented as a computer-based or processor-based component. For simplicity and ease of illustration, FIG. 2 depicts only one mobile device 204. In practice, however, the system 200 is suitably configured to support a plurality of mobile devices 204, where the patient or user owns or operates at least one of the supported mobile devices 204. An exemplary embodiment of a device suitable for implementing the mobile device 204 is described below with reference to FIG. 3.

The remainder of this description assumes that the mobile device 204 is a smartphone used by the particular patient. To this end, the configuration and general functionality of the mobile device 204 can be substantially consistent with conventional smartphone design. In this regard, a suitably designed mobile app is installed on the mobile device 204 to allow the patient to receive, view, and interact with messages and notifications provided by the system. The mobile app installed on the mobile device 204 can also be utilized to provide relevant data to other systems (not illustrated) for storage and analysis. For example, the mobile app can manage and upload the following information, without limitation: calendar data (time of day, day of the week, month, season, etc.); user profile data; GPS data that indicates the geographic position of the mobile device 204; map or navigation data associated with operation of the mobile device 204; user-entered meal consumption, food content, and/or food ingredient data; user-entered carbohydrate data; user-entered exercise related data; user-entered medication related data; user response data associated with the receipt of glycemic insight messages; user feedback related to glycemic insight messages; accelerometer data; contacts list information; web browser data; consumer purchasing data; and the like.

In certain embodiments, the insulin infusion device 206 is a portable patient-worn or patient-carried component that is operated to deliver insulin into the body of the patient via, for example, an infusion set. In accordance with certain exemplary embodiments, each insulin infusion device 206 supported by the system 200 is implemented as a computer-based or processor-based component. For simplicity and ease of illustration, FIG. 2 depicts only one insulin infusion device 206. In practice, however, the system 200 is suitably configured to support a plurality of insulin infusion device 206, wherein each patient or user owns or operates at least one of the insulin infusion devices 206. An exemplary embodiment of a device suitable for implementing the insulin infusion device 206 is described below with reference to FIG. 3.

The system 200 obtains input data from one or more sources, which may include various diabetes management devices (an insulin infusion device, a continuous glucose monitoring device, a glucose sensor, a monitor device, or the like). In this regard, the insulin infusion device 206 represents a source of input data for the system 200. In certain embodiments, the insulin infusion device 206 provides data that is associated with its operation, status, insulin delivery events, and the like. As mentioned previously, relevant data generated or collected by the insulin infusion device 206 can be transmitted directly or indirectly to other components of the system including the data uploader component 212, depending on the particular implementation of the system 200. The particular type of data provided by the insulin infusion device 206 is described in more detail below.

The patient or user can own or operate the blood glucose meter 208. The blood glucose meter 208 is configured to measure the blood glucose level of a user by analyzing a blood sample. For example, the blood glucose meter 208 may include a receptacle for receiving a blood sample test strip. In this regard, the user inserts a test strip into the blood glucose meter 208, which analyzes the sample and displays a blood glucose level corresponding to the test strip sample. The blood glucose meter 208 may be configured to communicate the measured blood glucose level to the insulin infusion device 206 for storage and processing, to the mobile device 204, or to the data uploader component 212. In some scenarios, the patient is responsible for entering each blood glucose measurement into the insulin infusion device 206. Ultimately, the measured blood glucose data can be provided to any components of the system for analysis.

The glucose sensor 210 can be owned or operated by the patient or user. The glucose sensor 210 is suitably configured to measure a glucose level (interstitial) of the patient in real time. The glucose sensor 210 may include a wireless transmitter that facilitates transmission of the sensor glucose data to other devices, such as the insulin infusion device 206 or the data uploader component 212 or other components of the system, where the sensor glucose data can be received for further processing.

Depending on the particular embodiment and application, the system 200 can include or cooperate with other devices, systems, and sources of input data. Devices within the system 200 may be configured to support the transmission of data to various external devices, such as, without limitation: a stationary monitor device, such as a bedside monitor or a piece of hospital monitoring equipment; a portable computer, such as a laptop PC, a palmtop PC, or a tablet PC; a stationary computer, such as a desktop PC; a personal digital assistant, which may also be a portable email device; one or more additional computing devices or databases; or the like. The above list of possible external devices is not exhaustive, and an implementation of the system 200 can be designed to accommodate communication with other systems, equipment, computing devices, components, and elements that are external to the system 200. For example, in certain embodiments the system 200 includes one or more sources of contextual information or data, which may include, without limitation: activity tracker devices; meal logging devices or apps; mood tracking devices or apps; and the like.

The system 200 includes a local infusion system having one or more local devices configured to wirelessly communicate with each other. This description may refer to the local infusion system as a "personal area network" or a "body area network" of its constituent devices. These local devices may be configured to transmit and receive local communications within the local infusion system, where such local communications are transmitted and received in accordance with one or more specified local data communication protocols. For example, local communications may be exchanged between local devices using one or more wireless data communication protocols (which may leverage RF, infrared, magnetic induction, or other wireless techniques) and/or using one or more wired data communication protocols. Thus, one or more of the local devices can be considered to be a wireless medical device in the context of this description. The local infusion system may be flexibly configured such that any given local device can communicate with any other local device, and a communication link or path between two local devices may be unidirectional or bidirectional. FIG. 2 depicts an exemplary embodiment where each communication link or path is bidirectional (represented by double headed arrows).

Figure 3:
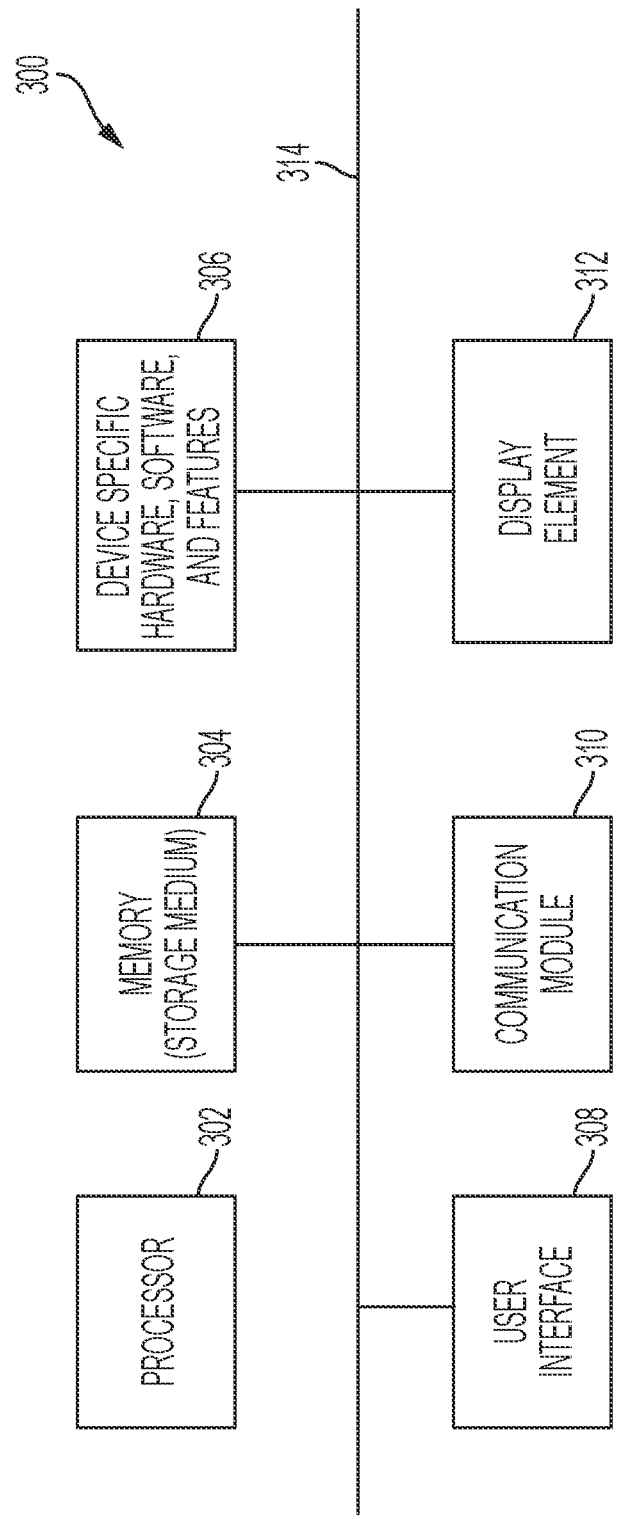
FIG. 3 is a simplified block diagram representation of an exemplary embodiment of a computer-based or processor-based device in accordance with the disclosed embodiments.

Moreover, the local devices in the local infusion system may be capable of communication (unidirectional or bidirectional) with one or more "external" devices that are not considered to be part of the local infusion system. The manner in which a given local device within the local infusion system communicates with a given external device may vary depending upon the particular configuration of the system 200, the characteristics of the local device, and the characteristics of the external device. For example, data may be routed between the local infusion system and an external device using one data communication network, using a plurality of data communication networks, using a direct wireless or wired connection, or the like As mentioned above, the system 200 includes or cooperates with computer-based and/or processor-based components having suitably configured hardware and software written to perform the functions and methods needed to support the features described herein. For example, the mobile device 204, the insulin infusion device 206, the blood glucose meter 208 and the data uploader component 212 can be realized as an electronic processor-based component. An exemplary embodiment of a device suitable for implementing the various components of the system will described below with reference to FIG. 3. In this regard, FIG. 3 is a simplified block diagram representation of an exemplary embodiment of a computer-based or processor-based device 300 that is suitable for deployment in the system shown in FIG. 2.

The illustrated embodiment of the device 300 is intended to be a high-level and generic representation of one suitable platform. In this regard, any of the computer-based or processor-based components of the system 200 can utilize the architecture of the device 300. The illustrated embodiment of the device 300 generally includes, without limitation: at least one processor 302; a suitable amount of memory 304; device-specific hardware, software, firmware, and/or features 306; a user interface 308; a communication module 310; and a display element 311. Of course, an implementation of the device 300 may include additional elements, components, modules, and functionality configured to support various features that are unrelated to the subject matter described here. For example, the device 300 may include certain features and elements to support conventional functions that might be related to the particular implementation and deployment of the device 300. In practice, the elements of the device 300 may be coupled together via a bus or any suitable interconnection architecture 301.

The processor 302 may be implemented or performed with a general-purpose processor, a content addressable memory, a digital signal processor, an application specific integrated circuit, a field programmable gate array, any suitable programmable logic device, discrete gate or transistor logic, discrete hardware components, or any combination designed to perform the functions described here. Moreover, the processor 302 may be implemented as a combination of computing devices, e.g., a combination of a digital signal processor and a microprocessor, a plurality of microprocessors, one or more microprocessors in conjunction with a digital signal processor core, or any other such configuration.

The memory 304 may be realized as RAM memory, flash memory, EPROM memory, EEPROM memory, registers, a hard disk, a removable disk, a CD-ROM, or any other form of storage medium known in the art. In this regard, the memory 304 can be coupled to the processor 302 such that the processor 302 can read information from, and write information to, the memory 304. In the alternative, the memory 304 may be integral to the processor 302. As an example, the processor 302 and the memory 304 may reside in an ASIC. At least a portion of the memory 304 can be realized as a computer storage medium, e.g., a tangible computer-readable medium having computer-executable instructions stored thereon. The computer-executable instructions, when read and executed by the processor 302, cause the device 300 to perform certain tasks, operations, functions, and processes that are specific to the particular embodiment. In this regard, the memory 304 may represent one suitable implementation of such computer-readable media. Alternatively, or additionally, the device 300 could receive and cooperate with computer-readable media (not separately shown) that is realized as a portable or mobile component or platform, e.g., a portable hard drive, a USB flash drive, an optical disc, or the like.

The device-specific hardware, software, firmware, and features 306 may vary from one embodiment of the device 300 to another. For example, the device-specific hardware, software, firmware, and features 306 will support: smartphone functions and features when the device 300 is realized as a mobile telephone; conventional personal computer functions and features if the device 300 is realized as a laptop or tablet computer; insulin pump operations when the device 300 is realized as an insulin infusion device; etc. In practice, certain portions or aspects of the device-specific hardware, software, firmware, and features 306 may be implemented in one or more of the other blocks depicted in FIGS. 3 and 4.

The user interface 308 may include or cooperate with various features to allow a user to interact with the device 300. Accordingly, the user interface 308 may include various human-to-machine interfaces, e.g., a keypad, keys, a keyboard, buttons, switches, knobs, a touchpad, a joystick, a pointing device, a virtual writing tablet, a touch screen, a microphone, or any device, component, or function that enables the user to select options, input information, or otherwise control the operation of the device 300. The user interface 308 may include one or more graphical user interface (GUI) control elements that enable a user to manipulate or otherwise interact with an application via the display element 311.

The communication module 310 facilitates data communication between the device 300 and other components as needed during the operation of the device 300. In the context of this description, the communication module 310 can be employed to transmit or stream device-related control data, patient-related data, device-related status or operational data, glycemic insight messages and notifications, and the like. It should be appreciated that the particular configuration and functionality of the communication module 310 can vary depending on the hardware platform and specific implementation of the device 300. Accordingly, the communication module 310 is utilized to obtain input data from various sources, and to send output data to other components or devices that are described above with reference to FIGS. 1 and 2. In practice, an embodiment of the device 300 may support wireless data communication and/or wired data communication, using various data communication protocols. For example, the communication module 310 could support one or more wireless data communication protocols, techniques, or methodologies, including, without limitation: RF; IrDA (infrared); Bluetooth®; ZigBee® (and other variants of the IEEE 802.15 protocol); IEEE 802.11 (any variation); IEEE 802.16 (WiMAX or any other variation); Direct Sequence Spread Spectrum; Frequency Hopping Spread Spectrum; cellular/wireless/cordless telecommunication protocols; wireless home network communication protocols; paging network protocols; magnetic induction; satellite data communication protocols; wireless hospital or health care facility network protocols such as those operating in the WMTS bands; GPRS; and proprietary wireless data communication protocols such as variants of Wireless USB. Moreover, the communication module 310 could support one or more wired/cabled data communication protocols, including, without limitation: Ethernet; powerline; home network communication protocols; USB; IEEE 2394 (Firewire); hospital network communication protocols; and proprietary data communication protocols. In one particular implementation, the communication module 310 includes a far-field communication module and a body area network communication module, and a controller (not illustrated).

The far-field communication module includes various far-field communication interfaces that can be used to communicate electromagnetic signals to other devices that are part of a body area network. In this non-limiting example, various far-field communication interfaces can include, but are not limited to, a Bluetooth low energy (BLE®) communication interface, a classical Bluetooth® (BT) communication interface, a wireless local area network (WLAN) communication interface (e.g., a Wi-Fi interface), and a cellular communication interface. The above-mentioned communication interfaces can comply with any known standards. For example, the BLE® communication interface can communicate in compliance with any Bluetooth® release (e.g., versions 1.0 through 5.1), and any physical (PHY) layer specifications defined therein. For instance, Bluetooth® 5.0 includes three PHY layer variations called LE 1M, LE 2M and LE Coded. Each PHY variant has its own particular characteristics and was designed with specific aims in mind. As another non-limiting example, the BLE® communication interface can communicate in compliance with a Bluetooth® mesh networking protocol (defined in Mesh Profile Specification and Mesh Model Specification which was adopted on Jul. 13, 2017). The Bluetooth® mesh networking protocol is a protocol based upon Bluetooth Low Energy® that allows for many-to-many communication over Bluetooth® radio.

When a signal from a far-field communication interface is transmitted by an antenna, it is attenuated over distance to the point that the signal cannot be effectively detected. This is called far-field transmission, and works well if the signal needs to be transmitted over a long distance. However, far-field communication interfaces can have problems if the wireless communication needs to be very low power and confines to a fairly short distance near body areas. Improper placement of devices close to a human body may result in a detuned antenna input impedance, reduced antenna efficiency, and distorted antenna radiation pattern. Penetration of electromagnetic signals generated by far-field communication interfaces into the human body is another problem because electromagnetic signals can be quickly absorbed and greatly attenuated due to the very conductive body tissues. In addition, interference can be very high due to coexistence of multiple far-field communication interfaces (e.g., BT, BLE®, Wi-Fi, and ZigBee®) that operate in the same frequency band. Power consumption can also limit continuous operation. Lastly, far-field communication interface can present potential security problems because electromagnetic signals can be intercepted and decrypted after propagating into free space.

On the other hand, the body area network communication module includes various near-field communication interfaces that can be used to communicate magnetic signals to other devices that are part of a body area network. In this non-limiting example, various near-field communication interfaces can include, but are not limited to, a near field magnetic inductive (NFMI) radio communication interface, a near-field electromagnetic induction (NFeMI) radio communication interface (not illustrated), a near field communication (NFC) interface, an RFID high-frequency (HF) communication interface, and one or more low power wide area network (LPWAN) communication interfaces. A near-field communication interface can provide a more reliable, a more secure, and a much lower power radio link within, on, and in the immediate proximity of a human body.

For example, NFMI is a short-range wireless technology that communicates using a tightly coupled magnetic field among devices. NFMI enables human body friendly, reliable, secure, and power efficient wireless communication. As used herein, the term "Near-Field Magnetic Induction (NFMI) radio communication system" can refer to a short range wireless physical layer that communicates by coupling a tight, low-power, non-propagating magnetic field between devices. A transmitter coil in one device can modulate a magnetic field which is measured by a receiver coil in another device. To explain further, in NFMI-based communication systems, a modulated signal that is sent out from a transmitter coil is in the form of a magnetic field. This magnetic field induces voltage on the receiving coil, which in turn will be measured by an NFMI receiver. NFMI radio communication systems differ from other wireless communications in that most conventional wireless RF systems use an antenna to generate, transmit, and propagate an electromagnetic wave, where all of the transmission energy is designed to radiate into free space. This type of transmission is referred to as "far-field." NFMI systems are designed to contain transmission energy within the localized magnetic field. This magnetic field energy resonates around the communication system, but does not radiate into free space. To explain further, the power density of NFMI signals attenuate at a rate inversely proportional to the distance to the sixth power compared to the second power for Bluetooth® signals. This means for the same distance, the power density of NFMI signals is 10000 times weaker than Bluetooth® signals provided that both transmitting power are equal. This type of wireless transmission is referred to as "near-field." Various modulation schemes used in typical RF communications (e.g., amplitude modulation, phase modulation, and frequency modulation) can also be used in near-field magnetic induction communication system.

As used herein, the term "near-field electromagnetic induction (NFeMI) radio communication interface" can refer to a communication interface that can operate near a human body by means of a combination of a magnetic field and electric field without the use of transversal radiating waves. Such NFEMI systems improve a wearable device's signal link budget and extend their range to a complete human body. Whereas RF wireless communication may be accomplished by propagating an RF plane wave through free space, NFEMI communication utilizes non-propagating quasi-static fields.

As used herein, the term "Near-field communication (NFC)" can refer to a set of communication protocols and data exchange formats that enable two or more electronic devices (e.g., a medical device such as an insulin pump and a portable device such as a smartphone) to establish communication with each other by bringing them within a short separation range of each other (e.g., 2 meters or less). NFC allows one- and two-way communication between endpoints, suitable for many applications. NFC uses electromagnetic induction between two loop antennas (located within each other's near-field) to effectively form an air-core transformer that allows them to exchange information. The NFC interface operates based on similar principles as the NFMI interface 322 and uses the same high-frequency (HF) band. However, NFMI extends the range of NFC (e.g., from a distance of 1-4 inches for NFC, to up to 9 feet for NFMI). At around 13 MHz, NFMI provides a data rate of over 400 Kbps per frequency channel, up to 10 separate frequency channels and 10 sub-channels per frequency channel using time division (e.g., a hundred separate wireless links inside a single WBAN). In one non-limiting implementation, NFC-enabled devices that are described herein can exchange information in accordance with any NFC standards that cover communications protocols and data exchange formats. NFC standards cover communications protocols and data exchange formats and are based on existing radio-frequency identification (RFID) standards including ISO/IEC 14443. The standards include ISO/IEC 18092 and those defined by the NFC Forum. In addition to the NFC Forum, the GSM Association (GSMA) group defined a platform for the deployment of GSMA NFC Standards within mobile handsets.

RFID systems can operate in low frequency (LF), high frequency (HF), and ultra-high frequency (UHF) bands, and thus can be categorized by the frequency band within which they operate: low frequency, high frequency, and ultra-high frequency. In addition, there are also two broad categories of systems—passive and active RFID. The LF band covers frequencies from 30 KHz to 300 KHz (e.g., some LF RFID systems operate at 125 KHz, while others operate at 134 KHz). The RFID HF communication interface 326 can operate in a RF band that ranges from 3 to 30 MHz, with communications ranges between 10 cm and 1 m. There are several HF RFID standards, such as the ISO 15693 standard for tracking items, and the ECMA-340 and ISO/IEC 18092 standards for Near Field Communication (NFC), the ISO/IEC 14443 A and ISO/IEC 14443 standards. The UHF frequency band covers the range from 300 MHz to 3 GHz, and the range of some UHF systems can be as long as 12 m with faster data transfer rates than LF or HF. The UHF frequency band is regulated by a single global standard called the ECPglobal Gen2 (ISO 18000-63) UHF standard.

The low power wide area network (LPWAN) communication interfaces can include interfaces such as a Long Term Evolution for Machines (LTE-M) communication interface (LTE-Cat M1) and/or a narrowband-IoT (NB-IoT) communication interface (not illustrated). NB-IOT and LTE-M are two newer low power wide area (LPWA) technologies that were developed for IOT applications. Both are protocols for low bandwidth cellular communications that connect to the internet devices that need to transmit small amounts of data, with the lower costs (both hardware and subscription) and the higher battery life.

The various communication interfaces mentioned above are non-limiting, and can be implemented in accordance with any known standards including those mentioned above. However, it should be appreciated that the number of communication interfaces that are included as part of the communication module 310 can vary depending on the implementation.

A controller (not illustrated) can be configured to control which ones of the communication interfaces are selected and used by a device or component of the wireless body area network to communicate data with other devices or components that are part of the wireless body area network. For example, the controller is configured to select which one of the communication interfaces is to be used at any particular time and switch between which one of the communication interfaces is enabled and used by a device or component of the wireless body area network to communicate data with other devices or components that are part of the wireless body area network.

As will be described in greater detail below, depending on a device's proximity to the body area network, the controller can select any of the various communication interfaces to use for communications with other devices that are part of the body area network. The controller can seamlessly switch between the various communication interfaces based on factors such as quality of service of the communication link with another device, the security type of the data that is being communicated to the other device, etc. In this regard quality of service can be measured using any standard quality of service performance metrics (e.g., RSSI, packet loss, packet error rate (PER), bit rate, bit error rate, latency, throughput, transmission delay, availability, jitter, etc.) and compared to a threshold. Quality of service metrics can also include metrics such as service response time, loss, signal-to-noise ratio, crosstalk, echo, interrupts, frequency response, and so on. Quality of service (QoS) is the description or measurement of the overall performance of a service, particularly the performance seen by the users of the network.

When the quality of service is greater than or equal to the threshold, the device can utilize a particular communication interface. When the quality of services is less than the threshold, the controller can then determine an appropriate communication interface to switch to that will achieve the desired quality of service that is greater than or equal to the threshold. In addition, in some embodiments, once the controller determines that the quality of service over one of the communication interfaces is greater than or equal to the threshold, the controller can also determine the type of data that is being communicated by the device, and if it is a high security datatype, the controller can also restrict communication to one of the body area network communication interfaces such that communications can only take place within traceable security boundary, as defined by the body area network, where the wireless energy has not degraded to a negligible level. In other words, when the type of data being communicated is a high security datatype, the controller will only utilize one of the body area network communication interfaces to help ensure security of the data that's being communicated.

Referring again to FIG. 3, the display element 311 is suitably configured to enable the device 300 to render and display various screens, insight messages, notifications, GUIs, GUI control elements, drop down menus, auto-fill fields, text entry fields, message fields, or the like. Of course, the display element 311 may also be utilized for the display of other information during the operation of the device 300, as is well understood. Notably, the specific configuration, operating characteristics, size, resolution, and functionality of the display element 310 can vary depending upon the practical implementation of the device 300. For example, if the device 300 is a laptop computer, then the display element 311 may be a relatively large monitor. Alternatively, if the device 300 is a cellular telephone device (e.g., smartphone), then the display element 311 may be a relatively small integrated display screen, such as a touch-sensitive screen.

Figure 4:
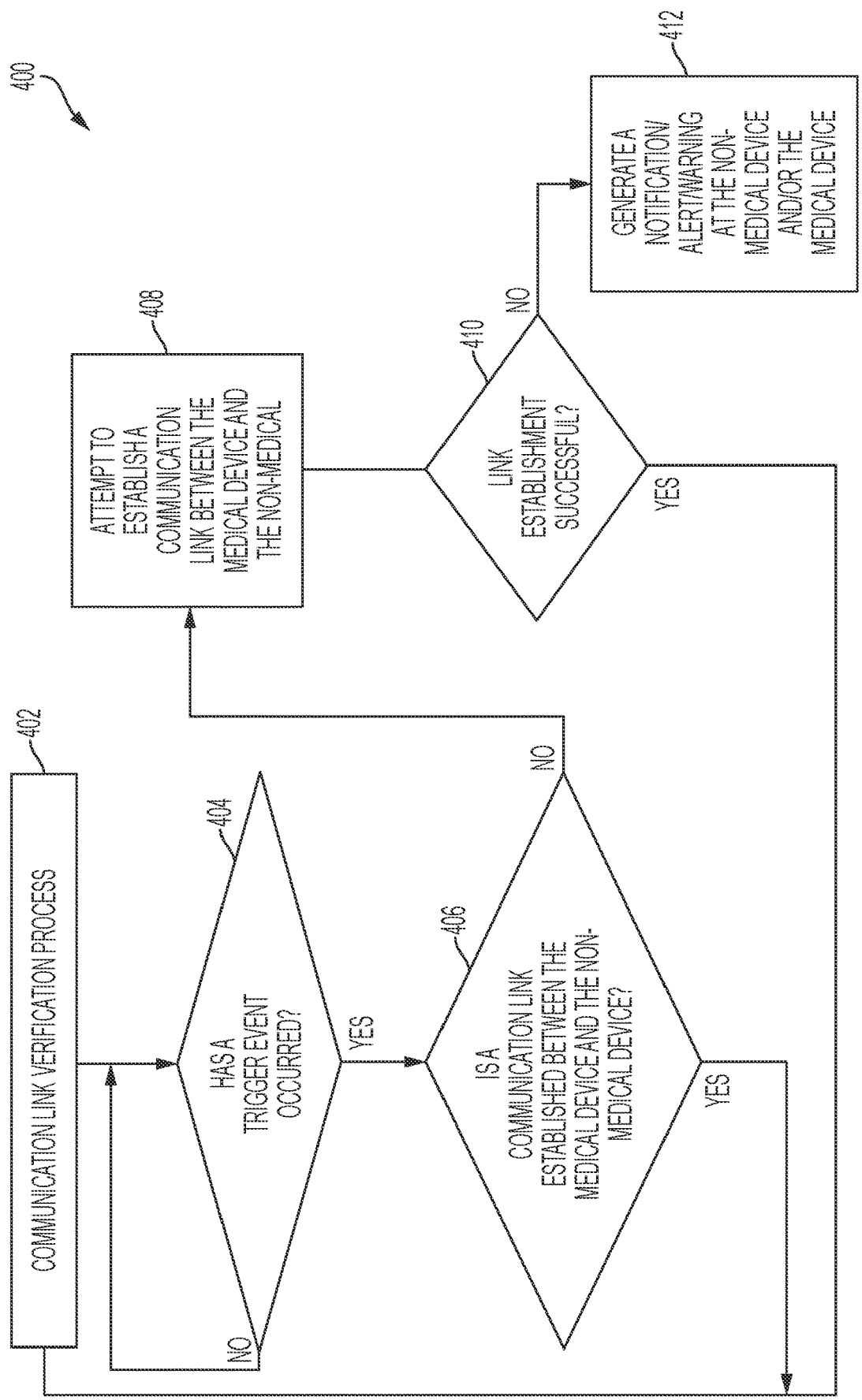
FIG. 4 is a method for verifying whether a communication link between a non-medical client device and a medical device is established and for causing a notification to be issued at a non-medical client device and/or a medical device when the communication link is not established in accordance with the disclosed embodiments.

FIG. 4 is a method 400 for verifying whether a communication link between a non-medical client device 108 and a medical device 102, 104 is established and for causing a notification to be issued at the non-medical client device 108 and/or the medical device 102, 104 when the communication link is not established in accordance with the disclosed embodiments. As a preliminary matter, it should be understood that the steps of the method 400 are not necessarily limiting. With reference to method 400, steps can be added, omitted, and/or performed simultaneously without departing from the scope of the appended claims. It should be appreciated that the method 400 may include any number of additional or alternative tasks, that the tasks shown in FIG. 4 need not be performed in the illustrated order, and that the method 400 may be incorporated into a more comprehensive procedure or process having additional functionality not described in detail herein. Moreover, one or more of the tasks shown in FIG. 4 could potentially be omitted from an embodiment of the method 400 as long as the intended overall functionality remains intact. It should also be understood that the illustrated method 400 can be stopped at any time. The method 400 is computer-implemented in that various tasks or steps that are performed in connection with the method 400 may be performed by software, hardware, firmware, or any combination thereof. For illustrative purposes, the following description of the method 400 may refer to elements mentioned above in connection with FIGS. 1-3.

In certain embodiments, some or all steps of this process, and/or substantially equivalent steps, are performed by execution of processor-readable instructions stored or included on a processor-readable medium. For instance, in the description of FIG. 4 that follows, the non-medical client device 108 and the medical device 102, 104 will be described as performing various acts, tasks or steps, but it should be appreciated that this refers to processing system(s) of these entities executing instructions to perform those various acts, tasks or steps. Depending on the implementation, the method 400 can be performed by an application at the non-medical client device 108 and/or an application at the medical device 102, 104 to regularly check the status of the communication link between the non-medical client device 108 and the medical device 102, 104 to make sure that the respective medical control applications at each are able to communicate. Therapy related notifications can be generated from the medical device 102, 104. Both the medical device 102, 104 and the non-medical client device 108 are capable of confirming communication link between them and notifying the user if the communication link is not there. If the communication link between the non-medical client device 108 and the medical device 102, 104 is not adequate (e.g., not established), one or more notifications, warnings, alerts or alarms on the medical device 102, 104 can be activated to alert the user that the communication link between the non-medical client device 108 and the medical device 102, 104 is inadequate. As described above, the notifications, warnings, alerts or alarms on the medical device 102, 104 can be, for example, visual, haptic and/or audio alarms. In some embodiments, the visual, haptic and/or audio alarms can be implemented in specific sequences of visual, audio and haptics for different messages. For example, three flashes or vibration followed by a pause to indicate loss of communication with non-medical client device 108. Furthermore, in the description of FIG. 4, a particular example is described in which the non-medical client device 108 and/or the medical device 102, 104 perform certain actions by interacting with other elements of the system described above with reference to FIGS. 1-3.

The communication link verification method 400 begins at 402, where the link verification process starts and the method 400 proceeds to 404. At 404, an application determines whether a trigger event has occurred. The trigger event could be, for example, receiving an indication that an alert has been issued or needs to be acknowledged; receiving an indication that a notification, alarm, alert, or warning needs to be activated; receiving an indication that a link verification timer has expired; receiving an indication that a link verification counter has a count greater than or equal to a threshold count; receiving that a regularly scheduled data transfer (e.g., blood glucose or confirmation of last insulin delivery) did not occur, etc. The method 400 loops at 404 until a trigger event occurs and then proceeds to 406.

At 406, the application determines whether the communication link between the non-medical client device 108 and the medical device 102, 104 is established or adequate (e.g., whether the medical control application 107 that is running on the non-medical client device 108 is able to communicate with the medical control application 105 that is running at the medical device 102, 104). When the application determines (at 406) that an adequate communication link is established between communication interfaces of the non-medical client device 108 and the medical device 102, 104, the method 400 loops back to 402. In one embodiment, a timer or counter can be reset when it is determined (at 406) that the non-medical client device 108 and the medical device 102, 104 have an adequate communication link.

When the application determines (at 406) that the that the communication link is inadequate, the method 400 proceeds to 408 where the application at either the non-medical client device 108 or the medical device 102, 104 attempts to establish (or reestablish) a communication link between communication interfaces of the medical device 102, 104 and the non-medical client device 108. The method 400 then proceeds to 410, where the application determines whether the communication link was successfully established. When the application determines (at 410) that the communication link was successfully established, the method 400 loops back to 402.

When the application determines (at 410) that the communication link was not successfully established, the method 400 proceeds to 412, where the application at the non-medical client device 108, and/or the application at the medical device 102, 104, causes one or more notifications, warnings, alarms or alerts to be activated at the non-medical client device 108, and/or the medical device 102, 104 causes one or more notifications, warnings, alarms or alerts to be activated at the medical device 102, 104. Since the non-medical client device 108 may be separated from the patient, the medical device 102, 104 should be able perform the check and if needed issue a notification. Having the non-medical client device 108 in the system may be critical in situations where the system is programmed to also notify the caregivers or health care providers thru the cloud.

Figure 5:
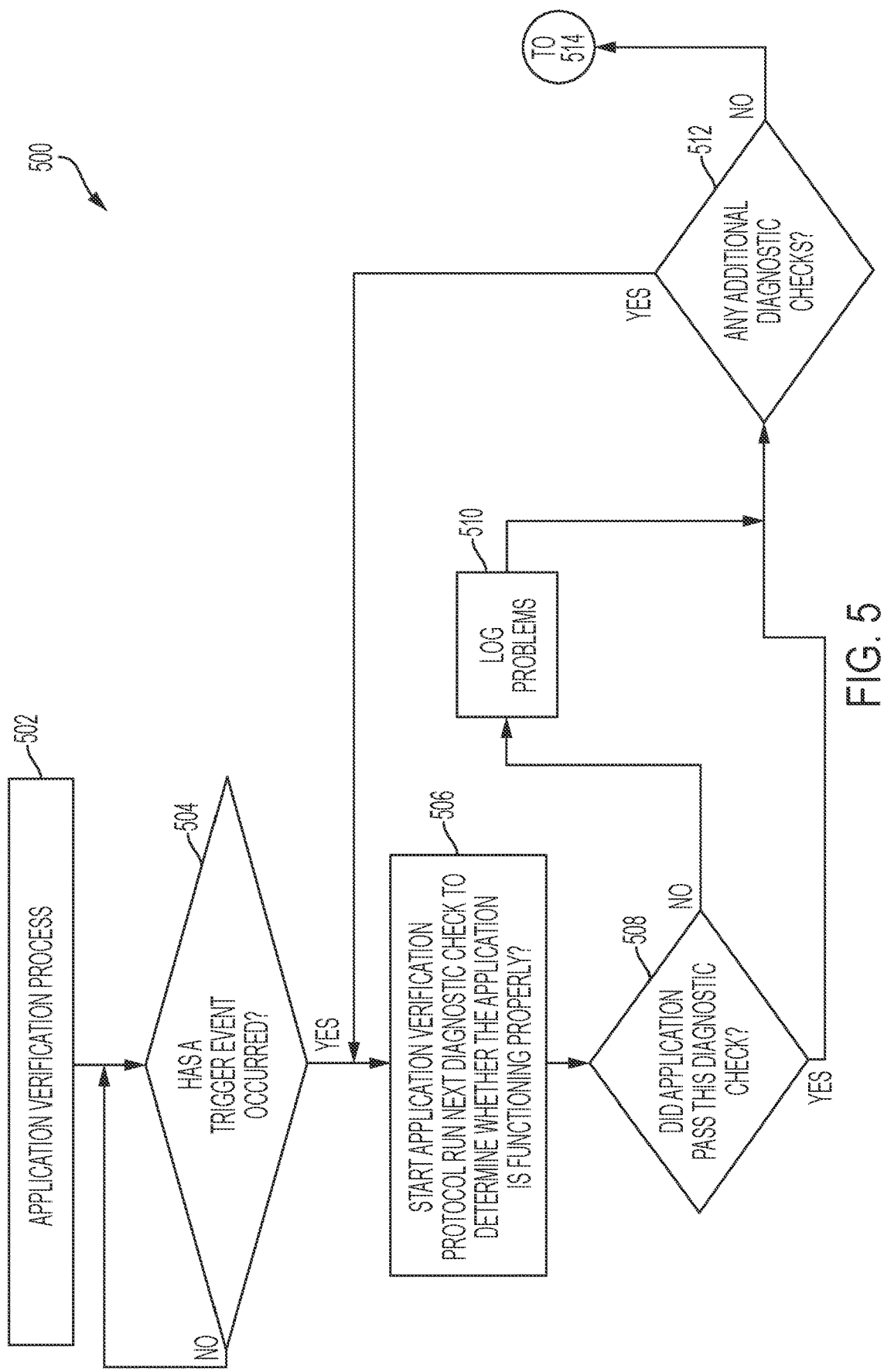
FIG. 5 is a method for verifying that a non-medical client device and a medical control application are operating/functioning properly in accordance with the disclosed embodiments.

FIG. 5 is a method 500 for verifying that a non-medical client device and a medical control application are operating/functioning properly in accordance with the disclosed embodiments. As a preliminary matter, it should be understood that the steps of the method 500 are not necessarily limiting. With reference to method 500, steps can be added, omitted, and/or performed simultaneously without departing from the scope of the appended claims. It should be appreciated that the method 500 may include any number of additional or alternative tasks, that the tasks shown in FIG. 5 need not be performed in the illustrated order, and that the method 500 may be incorporated into a more comprehensive procedure or process having additional functionality not described in detail herein. Moreover, one or more of the tasks shown in FIG. 5 could potentially be omitted from an embodiment of the method 500 as long as the intended overall functionality remains intact. It should also be understood that the illustrated method 500 can be stopped at any time. The method 500 is computer-implemented in that various tasks or steps that are performed in connection with the method 500 may be performed by software, hardware, firmware, or any combination thereof. For illustrative purposes, the following description of the method 500 may refer to elements mentioned above in connection with FIGS. 1-3.

In certain embodiments, some or all steps of this process, and/or substantially equivalent steps, are performed by execution of processor-readable instructions stored or included on a processor-readable medium. For instance, in the description of FIG. 5 that follows, the non-medical client device 108 and the medical device 102, 104 will be described as performing various acts, tasks or steps, but it should be appreciated that this refers to processing system(s) of these entities executing instructions to perform those various acts, tasks or steps. Depending on the implementation, the method 500 can be performed by an application at the non-medical client device 108 and/or at the medical device 102, 104. In one embodiment, the method 500 can be initiated by the non-medical client device 108 to execute one or more diagnostic checks to ensure the medical control application at the non-medical client device 108 is running properly and has access to required resources for its proper function. The method 500 can be used to generate a notification at the non-medical client device 108 to alert the user when medical control application 107 of the non-medical client device 108 is not operating/functioning properly (e.g., not running properly or does not have access to required resources for it to function properly). Furthermore, in the description of FIG. 5, a particular example is described in which the non-medical client device 108 and/or the medical device 102, 104 perform certain actions by interacting with other elements of the system described above with reference to FIGS. 1-3.

The method 500 starts at 502, the application starts an application verification process. At 504, the application monitors for a trigger event by determining whether a trigger event has occurred. The trigger event could be, for example, receiving an indication that an alert has been issued or needs to be acknowledged; receiving an indication that a notification, alarm, alert, or warning needs to be activated; receiving an indication that an application verification timer has expired; receiving an indication that an application verification counter has a count greater than or equal to a threshold count; receiving an indication or discovering that a communication link between the medical device and non-medical device is not operating or communicating as intended, etc. The method 500 loops at 504 until a trigger event occurs and then proceeds to 506.

When a trigger event has been determined to have occurred (at 504), the application initiates an application verification protocol at 506 to verify whether the application is operating/functioning properly and/or has access to required computing resources. The application verification protocol can include running one or more diagnostic checks. The diagnostic checks can be used to verify that the application is operating/functioning properly and/or has access to required computing resources.

The diagnostic checks that are performed or executed at 506 can include: verifying whether a communication link between a non-medical client device 108 and a medical device 102, 104 is established (as described above with reference to FIG. 4); determining whether the application and/or the operating system version is up-to-date and/or authentic; determining whether the settings of the application are correct; determining whether the application is loading properly; determining whether the application is running properly; determining whether the application has access to adequate computing resources (e.g., processing resources, communication resources, user interface resources, and/or memory resources) of the device; determining whether the application has access to adequate computing resources of the non-medical client device 108 (e.g., processing resources, communication resources, user interface resources, and/or memory resources) of the device, etc. For instance, the medical device 102, 104 should be satisfied that the application is working properly and has access to resources such as processor, memory, speakers, camera flash, display, haptic or other vibrators, or other means for generating notifications, etc. If the medical device 102, 104 does have confirmation of this is should notify the user thru its own notification means. The number of diagnostic checks that are performed, and the order in which they are performed, can vary depending on the implementation.

In one embodiment, the diagnostic checks can be performed in parallel or simultaneously or nearly simultaneously. In another embodiment, the diagnostic checks can be performed sequentially (in a predetermined order). For instance, after initiation of the application verification protocol at 506, steps 506 through 512 are iteratively performed to run a series of diagnostic checks that are used to determine whether the application is running or operating/functioning properly and/or has access to required computing resources. On the first iteration of 506, the first diagnostic check is executed. At 508, the application determines whether the application passed the first diagnostic check, and if so, the method 500 proceeds to 512, where the application determines whether there are any additional diagnostic checks to be executed. If it is determined (at 512) that there are no additional diagnostic checks to be executed, the method 500 proceeds to 514. When it is determined (at 512) that there are additional diagnostic checks to be executed, the method 500 loops back to 506, where the application executes the next diagnostic check to determine whether the application is operating/functioning properly and/or has access to required computing resources. In one embodiment, steps 506 through 512 loop until all the diagnostic checks have been executed.

Whenever the application determines at 508 that the application did not pass a particular diagnostic check that was executed (at 506), the method 500 can proceed to 510 where a problem corresponding to that particular diagnostic check is logged to create a record that explains why the application is not operating/functioning properly and/or does not have access to required computing resources, and the method then proceeds to 512. When it is determined (at 512) that there are no additional diagnostic checks to be executed, the method 500 proceeds to 514.

At 514, the application attempts to initiate one or more remedial correction measures in an attempt to correct issues that are causing it to run improperly so that the application will function correctly and/or have access to required computing resources. The remedial correction measures that are taken (at 514) can vary depending on the implementation and which diagnostic checks were performed or executed at 506, and which ones of those were determined to have not passed (NO at 508). The remedial correction measures that are taken (at 514) can include, for example: automatically closing and restarting the application; prompting the user to change restart the application of the non-medical client device when it is determined that the application is not loading or is not running properly; automatically powering the device off, restarting it and reopening the application; downloading and installing an up-to-date version of the application or the operating system when it is determined that the existing versions were not correct (e.g., no up-to-date and/or authentic); prompting the user to change one or more settings of the application when it is determined that one or more settings of the application are incorrect; freeing up additional computing resources for use by the application when it is determined that the application does not have access to adequate computing resources; changing a setting at the non-medical client device 108 (e.g., changing a setting via the operating system of the non-medical client device 108), etc.

Each time one of the remedial correction measures is initiated (at 514), the method 500 determines at 516 whether that correction measure was successful. Whenever any one of the remedial correction measures is determined (at 516) to have not been successful, this means that the application is not running properly and/or does not have access to required computing resources, and the method 500 can proceed to 518 where the application causes a notification (e.g., an alert, alarm or other warning signal) to be generated at the non-medical client device and/or at the medical device 102, 104. For example, an alert or notification could be issued at the infusion device 102. Alerts or notifications can be issued until the medical device 102, 104 is satisfied that the non-medical client device 108 and its corresponding application are working properly (e.g., able to communicate with the medical device 102, 104, issue notifications, etc.) In addition, in some embodiments, at 520, the non-medical client device 108 can present (e.g., via a display) suggestions to the user to suggest changes to settings on the non-medical client device 108 to correct the problem. For instance, the non-medical client device 108 can display suggested changes to notification settings, allow access to location data, activity data, a microphone of the non-medical client device 108, or provide shortcuts or links to settings that need to be changed. If the medical device 102, 104 fails, the non-medical client device 108 may suggest actions based last uploaded data such as insulin on board, last bolus, BG, etc. The suggestions may include instructions on how to use an insulin pen or syringe until the pump can be replaced. The non-medical client device 108 can also send notifications to care giver or health care provided (HCP).

When it is determined that each of the correction measures that were executed (at 514) were successful, this means that the application is running properly and/or has access to required computing resources, and the method 500 loops back to 504.

Figure 6:
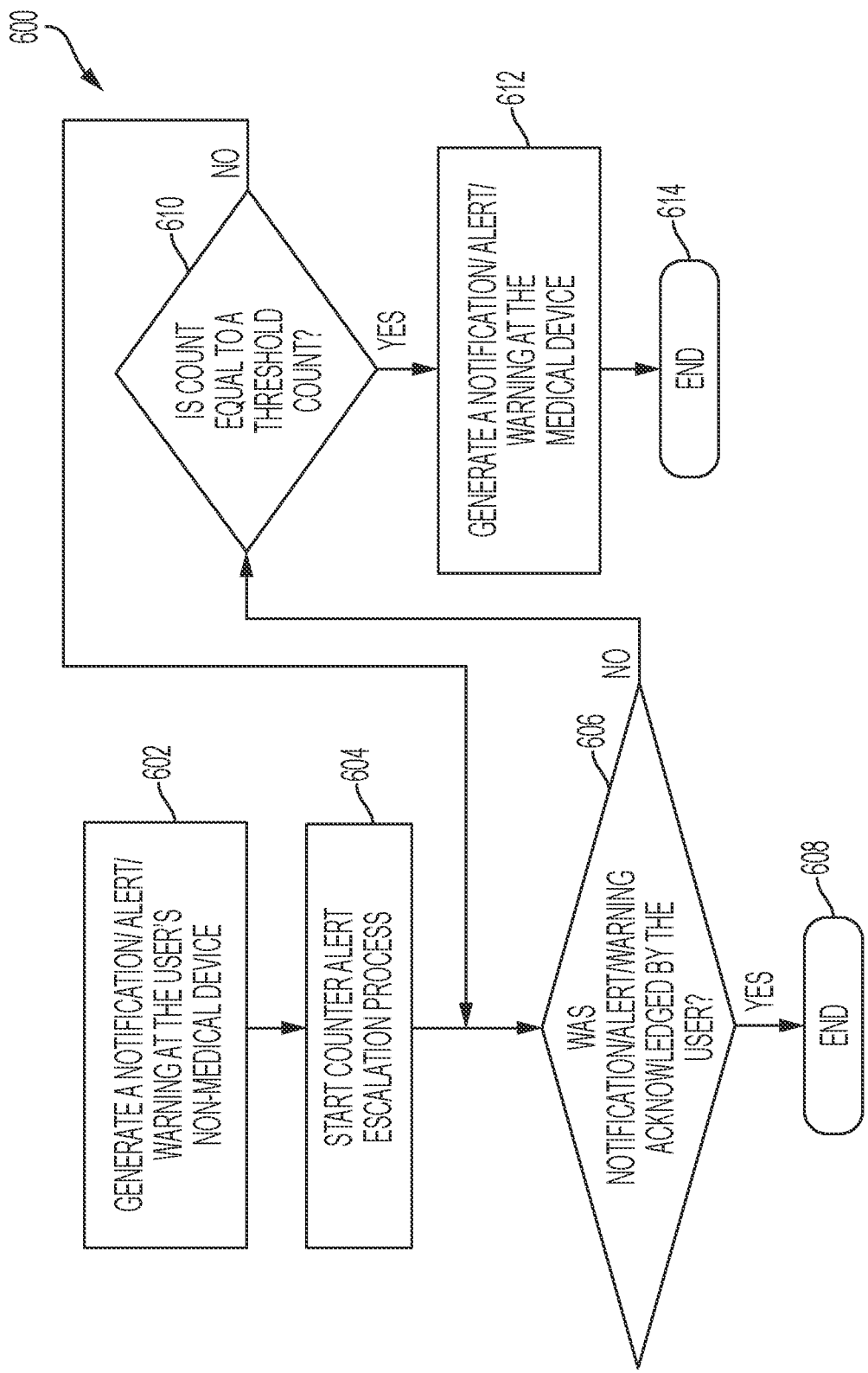
FIG. 6 is a method for generating a notification at a medical device when a notification generated at a non-medical client device is not acknowledged in accordance with the disclosed embodiments.

FIG. 6 is a method 600 for generating a notification (alarms, alert or other warning signal) at a medical device 102, 104 when a notification generated at a non-medical client device 108 is not acknowledged in accordance with the disclosed embodiments. As a preliminary matter, it should be understood that the steps of the method 600 are not necessarily limiting. With reference to method 600, steps can be added, omitted, and/or performed simultaneously without departing from the scope of the appended claims. It should be appreciated that the method 600 may include any number of additional or alternative tasks, that the tasks shown in FIG. 6 need not be performed in the illustrated order, and that the method 600 may be incorporated into a more comprehensive procedure or process having additional functionality not described in detail herein. Moreover, one or more of the tasks shown in FIG. 6 could potentially be omitted from an embodiment of the method 600 as long as the intended overall functionality remains intact. It should also be understood that the illustrated method 600 can be stopped at any time. The method 600 is computer-implemented in that various tasks or steps that are performed in connection with the method 600 may be performed by software, hardware, firmware, or any combination thereof. For illustrative purposes, the following description of the method 600 may refer to elements mentioned above in connection with FIGS. 1-3.

In certain embodiments, some or all steps of this process, and/or substantially equivalent steps, are performed by execution of processor-readable instructions stored or included on a processor-readable medium. For instance, in the description of FIG. 6 that follows, the non-medical client device 108 and the medical device 102, 104 will be described as performing various acts, tasks or steps, but it should be appreciated that this refers to processing system(s) of these entities executing instructions to perform those various acts, tasks or steps. The method 600 can be performed by applications at the non-medical client device 108 and at the medical device 102, 104. The method 600 can be used to generate a therapy-related notifications (e.g., a haptic signal, a visual signal and/or the audio signal) at the medical device 102, 104 to alert the user when alarms or alerts generated at the non-medical client device 108 are not acknowledged within a predetermined time threshold. Furthermore, in the description of FIG. 6, a particular example is described in which the non-medical client device 108 and/or the medical device 102, 104 perform certain actions by interacting with other elements of the system described above with reference to FIGS. 1-3.

To explain further, the method 600 begins at 602 (which can be step 518 of FIG. 5) when a notification (alarm, alert, or other warning signal) is generated at the user's non-medical client device. The method 600 then proceeds to 604, where an application at the non-medical client device 108 starts a counter for an alert escalation process, and the method then proceeds to 606. At 606, an application at the non-medical client device 108 determines whether the notification (generated at 602) at the non-medical client device 108 was acknowledged within a certain time frame. When it is determined that the notification (generated at 602) at the non-medical client device 108 was acknowledged within a certain time frame, the method 600 proceeds to 608 where the method 600 ends. When it is determined that the notification (generated at 602) at the non-medical client device 108 was not acknowledged within a certain time frame, the method 600 proceeds to 610.

At 610, the application at the non-medical client device 108 determines whether counter for the alert escalation process it greater than or equal to a threshold count. The process at 610 loops back to 606 until the counter for the alert escalation process is determined (at 610) to be equal to the threshold count. In other words, when the application determines (at 610) that the counter has not yet reached the threshold (e.g., count of the counter is less than the threshold), the method 600 loops back to 606.

When the counter for the alert escalation process is determined (at 610) to be equal to the threshold count, the method 600 proceeds to 612, where the application causes a notification (e.g., an alarm or alert) to be generated at the medical device 102, 104. In one embodiment, the medical control application 105 at the medical device 102, 104 causes a notification (e.g., an alert or alarm such as a haptic signal, visual signal and/or audio signal) to be generated at the medical device 102, 104. In one embodiment, the application can also activate haptics, camera flash, override silent mode, and increase speaker or alarm volume at the non-medical client device 108 if user does not acknowledge a notification. The method 600 proceeds to 614, where the method 600 ends. The notification is used to alert the user that notifications generated at the non-medical client device 108 have not been acknowledged so that the user can then take remedial measures at the non-medical client device 108 so that the application of the non-medical client device 108 is operating/functioning properly.

Thus, the medical device 102, 104 should initiate system checks for the non-medical client device 108. If the non-medical client device 108 is not functioning properly and cannot be fixed automatically or by the patient, notifications thru non-medical client device 108 should be generated. If notification is not acknowledged by patient on non-medical client device 108 then medical device 102, 104 should notify the patient. When notifications generated by medical device 102, 104 are not generated at the non-medical client device 108 (due to issues at the non-medical client device 108), the application 107 at the non-medical client device 108 can confirm whether the notifications have been acknowledged and send a confirmation to medical device 102, 104. If the non-medical client device 108 cannot confirm that a notification was issued, it should try to correct by checking settings to see if it has access to resources (speakers, haptics, etc.), and if not suggest corrective action. If corrective action is not successful, then a notification at can be generated at one or more of the medical devices 102, 104. The medical device 102, 104 can notify the user if acknowledgement from the non-medical client device 108 is not received within a reasonable time that can vary depending on criticality of notification. For example, an alert time to do a blood glucose check issued from medical device 102, 104 may allow more time for the non-medical client device 108 to come back with an acknowledgment or correct an issue. For critical alarms such as an occlusion in line, the allowed time can be shorter.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A processor-implemented method comprising:
generating a first notification via a medical application executing on a non-medical device, wherein the non-medical device is not configured to detect a medical condition of a user;
determining that the first notification was not acknowledged within a predetermined time frame;
verifying, in response to determining that the first notification was not acknowledged within the predetermined time frame, whether the medical application has access to user interface resources of the non-medical device; and
causing delivery of a second notification at a medical device attached to a body of the user to notify the user that the first notification has not been acknowledged.

2. The processor-implemented method of claim 1, wherein the user interface resources of the non-medical device include a speaker, haptics, or both the speaker and the haptics.

3. The processor-implemented method of claim 1, further comprising, based on determining that the first notification was not acknowledged within the predetermined time frame, performing:
increasing a speaker volume of the non-medical device;
overriding a silent mode of the non-medical device;
activating haptics at the non-medical device;
activating a camera flash at the non-medical device; or
a combination thereof.

4. The processor-implemented method of claim 1, wherein determining that the first notification was not acknowledged within the predetermined time frame comprises determining that a counter has reached a threshold count.

5. The processor-implemented method of claim 1, wherein the second notification comprises:
a haptic signal;
a visual signal;
an audio signal; or
a combination thereof.

6. The processor-implemented method of claim 1, wherein the non-medical device comprises a smartphone, a laptop, or a tablet.

7. The processor-implemented method of claim 1, wherein the medical device includes an insulin delivery device or a glucose sensor arrangement.

8. The processor-implemented method of claim 1, wherein the first notification comprises an audio, haptic, or visual warning signal.

9. The processor-implemented method of claim 1, wherein the first notification indicates that:
the medical application is not running properly;

the medical application does not have access to a computing resource;
a remedial correction measure is unsuccessful; or
a combination thereof.

10. A system comprising:
one or more processors; and
one or more processor-readable media storing instructions which, when executed by the one or more processors, cause performance of operations comprising:
generating a first notification via a medical application executing on a non-medical device, wherein the non-medical device is not configured to detect a medical condition of a user;
determining that the first notification was not acknowledged within a predetermined time frame;
verifying, in response to determining that the first notification was not acknowledged within the predetermined time frame, whether the medical application has access to user interface resources of the non-medical device; and
causing delivery of a second notification at a medical device attached to a body of the user to notify the user that the first notification has not been acknowledged.

11. The system of claim 10, wherein the user interface resources of the non-medical device include a speaker, haptics, or both the speaker and the haptics.

12. The system of claim 10, wherein the operations further comprise, based on determining that the first notification was not acknowledged within the predetermined time frame, performing:
increasing a speaker volume of the non-medical device;
overriding a silent mode of the non-medical device;
activating haptics at the non-medical device;
activating a camera flash at the non-medical device; or
a combination thereof.

13. The system of claim 10, wherein determining that the first notification was not acknowledged within the predetermined time frame comprises determining that a counter has reached a threshold count.

14. The system of claim 10, wherein the second notification comprises:
a haptic signal;
a visual signal;
an audio signal; or
a combination thereof.

15. The system of claim 10, wherein the first notification indicates that:
the medical application is not running properly;
the medical application does not have access to a computing resource;
a remedial correction measure is unsuccessful; or
a combination thereof.

16. One or more non-transitory processor-readable media storing instructions which, when executed by one or more processors, cause performance of operations comprising:
generating a first notification via a medical application executing on a non-medical device, wherein the non-medical device is not configured to detect a medical condition of a user;
determining that the first notification was not acknowledged within a predetermined time frame;
verifying, in response to determining that the first notification was not acknowledged within the predetermined time frame, whether the medical application has access to user interface resources of the non-medical device; and
causing delivery of a second notification at a medical device attached to a body of the user to notify the user that the first notification has not been acknowledged.

17. The one or more non-transitory processor-readable media of claim 16, wherein the operations further comprise, based on determining that the first notification was not acknowledged within the predetermined time frame:
increasing a speaker volume of the non-medical device;
overriding a silent mode of the non-medical device;
activating haptics at the non-medical device;
activating a camera flash at the non-medical device; or
a combination thereof.

18. The one or more non-transitory processor-readable media of claim 16, wherein determining that the first notification was not acknowledged within the predetermined time frame comprises determining that a counter has reached a threshold count.

19. The one or more non-transitory processor-readable media of claim 16, wherein the second notification comprises:
a haptic signal;
a visual signal;
an audio signal; or
a combination thereof.

* * * * *